United States Patent [19]

Hagen et al.

[11] Patent Number: 4,797,148

[45] Date of Patent: Jan. 10, 1989

[54] QUINOLINE DERIVATIVES AND THEIR USE FOR CONTROLLING UNDESIRABLE PLANT GROWTH

[75] Inventors: Helmut Hagen, Frankenthal; Ulrich Eichenauer, Frankfurt; Peter Plath, Frankenthal; Norbert Meyer, Ladenburg; Bruno Wuerzer, Otterstadt, all of Fed. Rep. of Germany

[73] Assignee: BASF Aktiengesellschaft, Ludwigshafen, Fed. Rep. of Germany

[21] Appl. No.: 933,795

[22] Filed: Nov. 24, 1986

[30] Foreign Application Priority Data

Nov. 26, 1985 [DE] Fed. Rep. of Germany ...... 3541722
Mar. 4, 1986 [DE] Fed. Rep. of Germany ...... 3606949

[51] Int. Cl.⁴ .................. C07D 215/48; A01N 43/42
[52] U.S. Cl. ........................... 71/94; 546/169; 71/88; 71/92; 71/90
[58] Field of Search ............... 546/169; 71/94

[56] References Cited

U.S. PATENT DOCUMENTS

| | | | |
|---|---|---|---|
| 4,497,651 | 2/1985 | Hagen et al. | 71/94 |
| 4,511,393 | 4/1985 | Hagen et al. | 71/92 |
| 4,522,646 | 6/1985 | Markert et al. | 546/169 |

Primary Examiner—Glennon H. Hollrah
Assistant Examiner—D. B. Springer
Attorney, Agent, or Firm—Keil & Weinkauf

[57] ABSTRACT

Quinoline derivatives of the formula

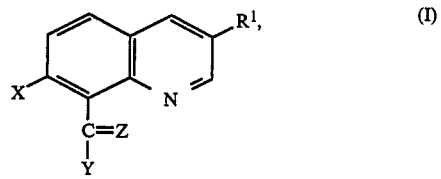

where $R^1$, X, Y and Z have the meanings given in the disclosure, herbicides containing these compounds as active ingredients, and a process for combating unwanted plant growth.

8 Claims, No Drawings

QUINOLINE DERIVATIVES AND THEIR USE FOR CONTROLLING UNDESIRABLE PLANT GROWTH

The present invention relates to novel quinoline derivatives, herbicides which contain these compounds as active ingredients, and a method for controlling undesirable plant growth using the novel compounds.

It has been disclosed that substituted quinolines possess herbicidal activity (DE-A Nos. 3 108 873, 3 210 979, 3 229 175 and 3 233 089).

We have found that quinoline derivatives of the formula 1

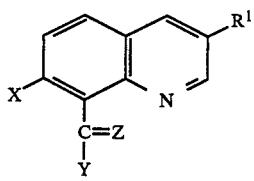

where $R^1$ is halogen or $C_1$–$C_4$-alkyl, X is halogen, Z is oxygen, hydroximino, $C_1$–$C_4$-alkoximino or a hydrazono radical which is substituted by $C_1$–$C_4$-alkyl, $C_2$–$C_5$-alkoxycarbonyl, arylsulfonyl, 1,3-oxazol-2-yl or 1,3-thiazol-2-yl, the last mentioned heterocyclic radicals in turn being substituted by $C_1$–$C_4$-alkyl, $C_2$–$C_4$-hydroxyalkyl or hydroxyl, and, where Z is oxygen, Y is a radical —$NR^2R^3$, in which $R^2$ is hydrogen and $R^3$ is $C_1$–$C_4$-hydroxyalkyl, $C_1$–$C_4$-alkoxy, $C_2$–$C_4$-alkenyl which is substituted by —C≡N or $C_2$–$C_5$-alkoxycarbonyl, unsubstituted or substituted arylsulfonyl, 1,3-oxazol-2-yl or 1,3-thiazol-2-yl, or in which $R^2$ and $R^3$ together form $C_1$–$C_4$-alkylidene which is substituted by $C_1$–$C_4$-dialkylamino, hydroxyamino or $C_1$–$C_4$-alkoxyamino; a hydrazino radical which is unsubstituted or substituted by $C_2$–$C_5$-alkylcarbonyl, $C_2$–$C_5$-alkoxycarbonyl, $C_1$–$C_4$-acyl, $C_2$–$C_6$-alkylidene, thiocarbamyl, $C_1$–$C_4$-alkoxyoxalyl or aminooxalyl or by arylsulfonyl which is unsubstituted or substituted by methyl, chlorine, bromine or nitro; $C_1$–$C_4$-alkyl which is unsubstituted or substituted by $C_2$–$C_5$-alkoxycarbonyl; or $C_3$–$C_8$-cycloalkenyl which is substituted by $C_1$–$C_4$-dialkylamino or $C_4$–$C_6$-alkyleneimino; where Z is $C_1$–$C_4$-alkoximino or the above substituted hydrazono radical, Y is hydrogen or halogen; and where Z is hydroximino, Y is halogen, amino, $C_1$–$C_4$-alkoxy or $C_1$–$C_4$-alkylthio which is substituted by carboxyl or $C_2$–$C_5$-alkoxycarbonyl, or in which the group

is the radical —C≡N⊕—O⊖ or a five-membered heterocyclic structure which, in addition to a nitrogen atom, also contains one or two further heteroatoms selected from the group consisting of nitrogen, oxygen and sulfur, and one or two double bonds, and is unsubstituted or substituted and/or fused to further carbocyclic or heterocyclic structures and bonded to the quinoline ring via a carbon atom, possess herbicidal activity.

In formula I, $R^1$ is, for example, fluorine, chlorine, bromine, methyl, ethyl, propyl, isopropyl, butyl, isobutyl, but-2-yl or tert-butyl, preferably chlorine or methyl.

In formula I, X is, for example, fluorine, chlorine or bromine, preferably chlorine.

In formula I, Z is, for example, oxygen, hydroximino, methoximino, ethoximino, propoximino, butoximino, methylhydrazono, ethylhydrazono, isopropylhydrazono, butylhydrazono, methoxycarbonylhydrazono, ethoxycarbonylhydrazono, propoxycarbonylhydrazono, tert-butoxycarbonylhydrazono, phenylsulfonylhydrazono, 2-methylphenylsulfonylhydrazono, 4-methylphenylsulfonylhydrazono, 4-chlorophenylsulfonylhydrazono, 4-methyl-1,3-thiazol-2-ylhydrazono, 4-ethyl-1,3-oxazol-2-ylhydrazono, 4-tert-butyl-1,3-thiazol-2-yl-hydrazono, 4-hydroxy-1,3-oxazol-2-ylhydrazono, 4-hydroxy-1,3-thiazol-2-ylhydrazono, 4-(2-hydroxyethyl)-1,3-thiazol-2-ylhydrazono or 3-(2-hydroxyethyl)-4-hydroxy-1,3-thiazol-2-ylhydrazono.

In formula I, the meaning of Y depends on the meaning of Z.

Where Z is oxygen, Y is, for example, 2-hydroxyethylamino, 1-methyl-2-hydroxyethylamino, 3-hydroxypropylamino, 1,1-dimethyl-2-hydroxyethylamino, methoxyamino, ethoxyamino, propoxyamino, isopropoxyamino, butoxyamino, isobutoxyamino, 2-cyano-2-methylethenylamino, 2-(methoxycarbonyl)-ethenylamino, 2-(ethoxycarbonyl)-2-methyle-thenylamino, 3-(ethoxycarbonyl)-prop-2-en-2-ylamino, phenylsulfonylamino, 2-methylphenylsulfonylamino, 4-methylphenylsulfonylamino, 4-chlorophenylsulfonylamino, 1,3-oxazol-2-ylamino, 1,3-thiazol-2-ylamino, dimethylaminomethylideneamino, 1-(dimethylamino)-ethylideneamino, hydroxyaminomethylideneamino, 1-(hydroxyamino)-ethylideneamino, methoxyaminomethylideneamino, 1-(ethoxyamino)-ethylideneamino, hydrazino, methoxycarbonylhydrazino, ethoxycarbonylhydrazino, isopropoxycarbonylhydrazino, tert-butoxycarbonylhydrazino, ethylidenehydrazino, prop-2-ylidenehydrazino, 2-methylbut-3-ylidenehydrazino, thiocarbamoylhydrazino, methoxyoxalylhydrazino, ethoxyoxalylhydrazino, aminooxalylhydrazino, phenylsulfonylhydrazino, 2-methylphenylsulfonylhydrazino, 4-methylphenylsulfonylhydrazino, 4-chlorophenylsulfonylhydrazino, 4-bromophenylsulfonylhydrazino, 4-nitrophenylsulfonylhydrazino, methyl, ethyl, propyl, butyl, ethoxycarbonylmethyl, 2-dimethylaminocyclopent-1-en-1-yl, 2-diethylaminocyclopent-1-en-1-yl, 2-pyrrolidinocyclopent-1-en-1-yl, 2-pyrrolidinocyclohex-1-en-1-yl or 2-piperidinocyclohex-1-en-1-yl.

Where Z is $C_1$–$C_4$-alkoximino or the abovementioned hydrazono radical, Y is, for example, hydrogen, chlorine or bromine.

Where Z is hydroximino, Y is, for example, chlorine, bromine, amino, methoxy, ethoxy, propoxy, isopropoxy, butoxy, isobutoxy, carboxymethylthio or ethoxycarbonylmethylthio.

The group

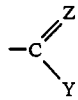

may furthermore be the radical —C≡N⊕—O⊖ or a five-membered heterocyclic structure. The latter may be substituted by $C_1$–$C_4$-alkyl, which is unsubstituted or substituted by hydroxyl or $C_1$–$C_4$-alkoxy, $C_1$–$C_4$-alkoxy, hydroxyl, amino, di-$C_1$–$C_4$-dialkylamino, $C_4$–$C_6$-alkyleneimino, $C_2$–$C_5$-alkoxycarbonyl, carbamyl or cyano and/or fused to carbocyclic structures, such as cyclopentane or cyclohexane or to heterocyclic structures, such as tetrahydrofuran or tetrahydropyran.

The following heterocyclic radicals may be mentioned as examples of the group

triazolyls, such as 1,3,4-triazol-2-yl or 1,2,4-triazol-3-yl, oxazolyls, such as 1,3-oxazol-2-yl or 1,2-oxazol-3-yl, thiazolyls, such as 1,3-thiazol-2-yl, oxadiazolyls, such as 1,3,4-oxadiazol-2-yl, partially hydrogenated oxazolyls, such as 4,5-dihydro-1,3-oxazol-1-yl or 4,5-dihydro-1,2-oxazol-3-yl, partially hydrogenated thiazolyls, such as 4,5-dihydro-1,3-thiazol-2-yl, substituted triazolyls, such as 5-methyl-1,3,4-triazol-2-yl, substituted oxazolyls, such as 4,5-dihydro-4-methyl-1,3-oxazol-2-yl, 4,5-dihydro-5-ethoxy-1,2-oxazol-3-yl, 5-methoxymethyl-1,2-oxazol-3-yl, 4-methoxycarbonyl-5-hydroxy-1,2-oxazol-3-yl, 4-methoxycarbonyl-5-methyl-1,2-oxazol-3-yl, 4,5-dihydro-5-hydroxymethyl-1,2-oxazol-3-yl, 4,5-dihydro-5-methyl-5-methoxycarbonyl-1,2-oxazol-3-yl, 4,5-dihydro-5-methoxycarbonyl-1,2-oxazol-3-yl, 4,5-dihydro-4,5-bis(methoxycarbonyl)-1,2-oxazol-3-yl (trans), 4,5-dihydro-4-cyano-5-amino-1,2-oxazol-3-yl, fused oxazolyls, such as 3a,4,5,6-tetrahydro-6a-pyrrolidinocyclopenta[d][1,2]oxazol-3-yl, 3a,4,5,6a-tetrahydrofuro[3,2-d][1,2]oxazol-3-yl, 3a,4,6,6a-tetrahydrofuro[3,4-d][1,2]oxazol-3-yl, 4H-3a,5,6,7a-tetahydropyrano[3,2-d][1,2]oxazol-3-yl, substituted thiazolyls such as 4,5-dihydro-4-methyl-1,3-thiazol-2-yl, substituted oxadiazolyls such as 5-ethyl-1,3,4-oxadiazol-2-yl, 5-hydroxy-1,3,4-oxadiazol-2-yl, 5-carbamyl-1,3,4-oxadiazol-2-yl or 3-methyl-1,2,4-oxadiazol-5-yl.

Preferred compounds are those in which $R^1$ and X are each halogen, in particular chlorine, Z is oxygen and Y is the radical —$NHR^3$, where $R^3$ is $C_1$–$C_4$-alkoxy, in particular ethoxy.

The novel carboxamides and carboxylic hydrazides (where Z is 0 and Y is $NR^2R^3$ or a hydrazino radical) are obtained by reacting the acid chloride (where Z is 0 and Y is Cl) with the appropriate amine or hydrazine in an inert solvent with the addition of an acid acceptor.

Suitable inert solvents are chlorohydrocarbons, such as methylene chloride or chlorobenzene, ethers, such as tetrahydrofuran, dioxane, 1,2-dimethoxyethane or diethylene glycol dimethyl ether, and aromatic hydrocarbons, such as toluene or xylene. 1,2-Dimethoxyethane and methylene chloride are preferred.

Suitable acid acceptors are tertiary amines, such as triethylamine, pyridine or N,N-dimethylaminopyridine. Advantageously, from 1 to 2 moles of acid acceptor are used per mole of acid chloride.

In some cases, it may also be advantageous to use an appropriate excess of the amine or hydrazine component as the acid acceptor. Triethylamine is preferably used.

The reaction temperature can be varied within a wide range. In general, the process is carried out at from −30° to +80° C., preferably from −10° to +25° C.

A possible method of preparing acid amides which possess the structural element

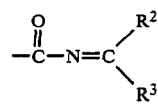

where $R^2$ and $R^3$ are each alkylidene, is to react the corresponding free amide with an amide acetal (e.g. N,N-dimethylformamide dimethyl acetal or N,N-dimethylacetamide dimethyl acetal) or an orthocarboxylate (e.g. trimethyl orthoformate or triethyl orthoacetate).

Suitable solvents are aliphatic amides, such as N,N-dimethylformamide or N,N-dimethylacetamide, and aromatic hydrocarbons, such as toluene, xylene or chlorobenzene. In some cases, it is also advantageous to carry out the reaction in excess amide acetal or orthocarboxylate. The alcohol formed during the reaction can be left in the reaction mixture or is preferably removed by means of distillation.

It is advantageous to choose as the reaction temperature the reflux temperature of the reaction mixture, which is generally from 100° to 150° C.

The keto compounds according to the invention can be obtained in a conventional manner from the carboxylate by means of a Grignard reaction; it is surprising that in this case the Grignard reaction stops at the keto stage, and no tertiary alcohol is formed. Those novel compounds which carry heterocyclic substituents can be obtained by conventional methods for synthesizing heterocycles, as described in, for example, R. A. Katritzky and C. W. Rees, Comprehensive Heterocyclic Chemistry, volumes 4 and 5, Pergamon Press 1984, and A. Weissberger, Chemistry of Heterocyclic Compounds, Interscience Publishers.

Where the group

is the radical —C≡N⊕—O⊖, the nitrile oxide is prepared starting from the oxime, via the hydroximic acid chloride intermediate, with subsequent elimination of hydrogen chloride.

The other compounds according to the invention (for example, oximes, hydrazones or oxime esters) can also be obtained by conventional methods, as described in, for example, Houben-Weyl, Methoden der organischen Chemie, volumes 10/2 and 10/4.

The quinoline derivatives I have a herbicidal action and are selective with respect to crops.

The quinoline derivatives of the formula I and the herbicides containing them can, for example, be applied in the form of directly atomizable solutions, powders, suspensions, including concentrated aqueous, oily or other suspensions or dispersions, emulsions, oil dispersions, pastes, dusting agents, broadcasting agents or granules, by spraying, misting, dusting, broadcasting or watering. Their application forms depend entirely on the intended uses; they should in any case ensure very fine distribution of the active ingredients according to the invention.

Mineral oil fractions having moderate to high boiling points, such as kerosene or diesel oil, coal tar oils and oils of vegetable or animal origin, aliphatic, cyclic and aromatic hydrocarbons, e.g. toluene, xylene, paraffin, tetrahydronaphthalene, alkylated naphthalenes or their derivatives, methanol, ethanol, propanol, butanol, cyclohexanol, cyclohexanone, chlorobenzene, isophorone or highly polar solvents, such as N,N-dimethylformamide, dimethylsulfoxide, N-methylpyrrolidone or water, are suitable for the preparation of directly atomizable solutions, emulsions, pastes or oil dispersions.

Aqueous forms for administration can be prepared from emulsion concentrates, dispersions, pastes, wettable powders, or water-dispersible granules by adding water. Emulsions, pastes or oil dispersions can be prepared if the substrates as such are dissolved in an oil or solvent are homogenized in water by means of wetting agents, adhesives, dispersants or emulsifiers. However, it is also possible to prepare water-dilutable concentrates which consist of active substance, wetting agents, adhesives, dispersants or emulsifiers and may contain solvents or oil.

Suitable surfactants are the alkali metal, alkaline earth metal and ammonium salts of aromatic sulfonic acids, for example ligninsulfonic acid, phenolsulfonic acid, naphthalenesulfonic acid and dibutylnaphthalenesulfonic acid, and of fatty acids, alkyl- and alkylarylsulfonates, alkylsulfates, lauryl ether sulfates and fatty alcohol sulfates, and salts of sulfated hexa-, hepta- and octadecanols and of fatty alcohol glycol ethers, condensates of sulfonated naphthalene and its derivatives with formaldehyde, condensates of naphhalene or of naphthalenesulfonic acids with phenol and formaldehyde, polyoxyethylene octylphenol ethers, oxyethylated isooctyl-, octyl- and nonylphenol, alkylphenol polyglycol ethers, tributylphenyl polyglycol ethers, alkylaryl polyether alcohols, isotridecyl alcohol, fatty alcohol/ethylene oxide condensates, oxyethylated castor oil, polyoxyethylene alkyl ethers, oxyethylated polyoxypropylene, lauryl alcohol polyglycol ether acetate, sorbitol esters, lignin sulfite waste liquors and methylcellulose.

Powders, broadcasting agents and dusting agents can be prepared by mixing or by milling the active substances together with a solid carrier.

Granules, e.g. coated granules, impregnated granules and homogeneous granules can be prepared by binding the active ingredients to solid carriers. The latter are mineral earths, such as silicas, silica gels, silicates, talc, kaolin, limestone, lime, chalk, bole, loess, clay, dolomite, diatomaceous earth, calcium sulfate, magnesium sulfate, magnesium oxide, ground plastics, fertilizers, such as ammonium sulfate, ammonium phosphate, ammonium nitrate and ureas, and vegetable products, such as grain flours, bark meal, wood flour and nutshell meal, cellulosic powders and other solid carriers.

The formulations contain from 0.1 to 95, preferably from 0.5 to 90% by weight of active ingredient.

Application may be effected by the preemergence or postemergence method, preferably the latter. If the active ingredients are less well tolerated by certain crops, application techniques may be used in which the herbicides are sprayed using sprayers in such a way that, as far as possible, the leaves of the sensitive crops remain unsprayed, while the active ingredients reach the leaves of undesirable plants growing underneath or the unoccupied soil surface (post-directed lay-by treatment).

The application rates of active ingredient are from 0.1 to 5.0, preferably from 0.25 to 3.0, kg/ha depending on the time of year, the target plants and the stage of growth.

In view of the action spectrum which can be covered in weed control, the toleration by crop plants or the desired effect on the growth of these plants, and in view of the wide range of methods of application, the novel compounds, depending on the pattern of substitution, can be employed in a large number of crops.

Examples of suitable crops are the following:

| Botanical name | Common name |
|---|---|
| *Allium cepa* | onions |
| *Ananas comosus* | pineapples |
| *Arachis hypogaea* | peanuts (groundnuts) |
| *Asparagus officinalis* | asparagus |
| *Avena sativa* | oats |
| *Beta vulgaris* spp. altissima | sugarbeets |
| *Beta vulgaris* spp. rapa | fodder beets |
| *Beta vulgaris* spp. esculenta | table beets, red beet |
| *Brassica napus* var. napus | rapeseed |
| *Brassica napus* var. napobrassica | swedes |
| *Brassica napus* var. rapa | turnips |
| *Brassica rapa* var. silvestris | turnip rape |
| *Camellia sinensis* | tea plants |
| *Carthamus tinctorius* | safflower |
| *Carya illinoinensis* | pecan trees |
| *Citrus limon* | lemons |
| *Citrus maxima* | grapefruits |
| *Citrus reticulata* | mandarins |
| *Citrus sinensis* | orange trees |
| *Coffea arabica* (*Coffea canephora, Coffea liberica*) | coffee plants |
| *Cucumis melo* | melons |
| *Cucumis sativus* | cucumbers |
| *Cynodon dactylon* | Bermudagrass |
| *Daucus carota* | carrots |
| *Elaeis guineensis* | oil palms |
| *Fragaria vesca* | strawberries |
| *Glycine max* | soybeans |
| *Gossypium hirsutum* (*Gossypium arboreum Gossypium herbaceum Gossypium vitifolium*) | cotton |
| *Helianthus annuus* | sunflowers |
| *Helianthus tuberosus* | Jerusalem artichoke |
| *Hevea brasiliensis* | rubber plants |
| *Hordeum vulgare* | barley |
| *Humulus lupulus* | hops |
| *Ipomoea batatas* | sweet potatoes |
| *Juglans regia* | walnut trees |
| *Lactua sativa* | lettuce |
| *Lens culinaris* | lentils |
| *Linum usitatissimum* | flax |
| *Lycopersicon lycopersicum* | tomatoes |
| *malus* spp. | apple trees |
| *Manihot esculenta* | cassava |
| *Medicago sativa* | alfalfa (lucerne) |
| *Mentha piperita* | peppermint |
| *Musa* spp. | banana plants |
| *Nicotiana tabacum* (*N. rustica*) | tobacco |
| *Olea europaea* | olive trees |
| *Oryza sativa* | rice |
| *Panicum miliaceum* | millet |
| *Phaseolus lunatus* | limabeans |
| *Phaseolus mungo* | mungbeans |
| *Phaseolus vulgaris* | snapbeans, grean beans, dry beans |
| *Pennisetum glaucum* | pearl millet |
| *Petroselinum crispum* spp. tuberosum | parsley |
| *Picea abies* | Norway spruce |
| *Abies alba* | fir trees |
| *Pinus* spp. | pine trees |
| *Pisum sativum* | English peas |

| Botanical name | Common name |
|---|---|
| *Prunus avium* | cherry trees |
| *Prunus domestica* | plum trees |
| *Prunus dulcis* | almond trees |
| *Prunus persica* | peach trees |
| *Pyrus communis* | pear trees |
| *Ribes sylvestre* | redcurrants |
| *Ribes uva-crispa* | gooseberries |
| *Ricinus communis* | castor-oil plants |
| *Saccharum officinarum* | sugar cane |
| *Secale cereale* | rye |
| *Sesamum indicum* | sesame |
| *Solanum tuberosum* | Irish potatoes |
| *Sorghum bicolor* (*s. vulgare*) | sorghum |
| *Sorghum dochna* | sorgho |
| *Spinacia oleracea* | spinach |
| *Theobroma cacao* | cacao plants |
| *Trifolium pratense* | red clover |
| *Triticum aestivum* | wheat |
| *Vaccinium corymbosum* | blueberries |
| *Vaccinium vitis-idaea* | cranberries |
| *Vicia faba* | tick beans |
| *Vigna sinensis* (*V. unguiculata*) | cow peas |
| *Vitis vinifera* | grapes |
| *Zea mays* | Indian corn, sweet corn, maize |

To increase the action spectrum and to achieve synergistic effects, the novel quinoline carboxylic acid derivatives may be mixed with numerous members of other groups of herbicidal or growth-regulating active ingredients, and may be applied together with these. Examples of suitable components of the mixtures are diazines, 4H-3,1-benzoxazine derivatives, benzothiadiazinones, N-phenylcarbamates, thiolcarbamates, halocarboxylic acids, triazines, amides, ureas, diphenyl ethers, triazinones, uracils, benzofuran derivatives, cyclohexanone-1,3-dione derivatives and others.

It may also be useful to apply the compounds of the formula I either alone or in combination with other herbicides, including further crop protection agents, for example agents for controlling pests or phytopathogenic fungi or bacteria. The compounds may also be mixed with mineral salt solutions which are used to remedy nutritional or trace element deficiencies. Nonphytotoxic oils and oil concentrates may also be added.

The Examples which follow illustrate the invention.

EXAMPLE 1

25 g (0.5 mole) of hydrazine hydrate and 50 g (0.5 mole) of triethylamine were dissolved in 500 ml of dimethoxyethane. 130 g (0.5 mole) of 3,7-dichloroquinoline-8-carbonyl chloride were slowly introduced into the solution, while cooling with ice, so that the temperature did not exceed 20° C. The mixture was stirred for 3 hours at room temperature, after which the solvent was removed in a rotary evaporator, the residue was taken up in water and the solution was filtered under suction. 101.5 g (79%) of 3,7-dichloroquinoline-8-carboxylic hydrazide of melting point 136° C. (compound No. 1) were obtained.

The following Examples in Table 1 were obtained in a similar manner.

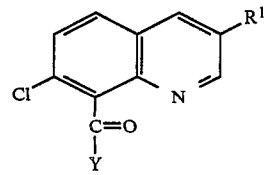

(Ia)

| Example No. Compound No. | $R^1$ | Y | Mp. [°C.] |
|---|---|---|---|
| 2 | Cl | —NH—NHCOCH$_3$ | 287 |
| 3 | CH$_3$ | —NH—NHCO$_2$C(CH$_3$)$_3$ | 120 |
| 4 | Cl | —NH—NHCOCONH$_2$ | 205 |
| 5 | Cl | —NH—NHCOCO$_2$C$_2$H$_5$ | 183 |
| 6 | Cl | —NH—NHCSNH$_2$ | 230 |
| 7 | Cl | —NH—NHSO$_2$C$_6$H$_4$CH$_3$ (p) | 210 |
| 8 | CH$_3$ | —NH—NH$_2$ | 205 |
| 9 | CH$_3$ | —NH—NHCOCONH$_2$ | 231 |
| 10 | CH$_3$ | —NH—NHCSNH$_2$ | 220 |
| 11 | CH$_3$ | —NH—NHSO$_2$C$_6$H$_4$CH$_3$ (p) | 228 |
| 12 | Cl | —NH—C(CH$_3$)$_2$CH$_2$OH | 215 |
| 13 | Cl | —NH—CH$_2$CH(CH$_3$)OH | 100 |
| 14 | Cl | —NH—CH$_2$CH$_2$OH | 179 |
| 15 | CH$_3$ | —NH—C(CH$_3$)$_2$CH$_2$OH | 165 |
| 16 | CH$_3$ | —NH—CH(CH$_3$)CH$_2$OH | 140 |
| 17 | CH$_3$ | —NH—CH$_2$CH$_2$OH | 168 |
| 18 | CH$_3$ | —NH—SO$_2$—C$_6$H$_5$ | 220 |
| 19 | Cl | —NH—SO$_2$—C$_6$H$_5$ | 163 |
| 20 | Cl | —NH—(thiazol-2-yl) | 260 |

EXAMPLE 21

O-Ethyl 3,7-dichloroquinoline-8-hydroxamate 13.0 g (50 millimoles) of 3,7-dichloroquinoline-8-carbonyl chloride were suspended in 50 ml of dimethoxyethane, and 5.8 g (60 millimoles) of 0-ethylhydroxyamine hydrochloride and 15 g (150 millimoles) of triethylamine were added. The mixture was stirred for 5 hours at room temperature, after which the solvent was removed in a rotary evaporator, the residue was triturated with water and the mixture was filtered under suction. 11.0 g (77%) of a product of melting point 140° C. were obtained (compound No. 21).

EXAMPLE 22

N,N-Dimethyl-N'-(7-chloro-3-methyl-8-quinoloyl)-formamidine 55.1 g (0.25 mole) of 7-chloro-3-methylquinoline-8-carboxamide were dissolved in 50 ml of N,N-dimethylformamide, 39.3 g (0.32 mole) of N,N-dimethylformamide dimethyl acetal were added, and the mixture was refluxed for 4 hours. After precipitation on ether, 44.0 g (64%) of colorless crystals of melting point 183°–185° C. (decomposition) were isolated (compound No. 22).

The following examples from Table 2 were obtained in a similar manner.

TABLE 2

(Ib) — structure: 7-chloroquinoline with R¹ at 3-position and C(=O)-Y at 8-position

| Example No. Compound No. | R¹ | Y | Mp. [°C.] |
|---|---|---|---|
| 23 | CH₃ | —N=C(CH₃)—N(CH₃)₂ | 141 |
| 24 | Cl | —N=C(CH₃)—N(CH₃)₂ | 205 |
| 25 | Cl | —N=CH—N(CH₃)₂ | 235 |

EXAMPLE 26

N-(7-Chloro-3-methyl-8-quinoloyl)-formamidoxime 13.8 g (50 millimoles) of the amidine from Example 22 were suspended in 50 ml of glacial acetic acid, 4.2 g (60 millimoles) of hydroxylammonium hydrochloride and 5.0 g (60 millimoles) of sodium acetate were added, and the mixture was refluxed for 5 hours, precipitated on water and filtered under suction. 6.0 g (45%) of a product of melting point 235°–238° C. were obtained (compound No. 26).

The corresponding 3-chloroquinoline compound was obtained in a similar manner (mp. 220°–230° C.; compound No. 27).

EXAMPLE 28

2-(7-Chloro-3-methylquinol-8-yl)-1,3,4-oxadiazole 12.0 g (50 millimoles) of 7-chloro-3-methylquinoline-8-carboxylic hydrazide (compound No. 8) in triethyl orthoformate were heated at 120° C. for 3 hours and the resulting alcohol was distilled off. Stripping off the excess ortho ester and trituration with ether gave 9.4 g (77%) of a product of melting point 165° C. (compound No. 28).

The compounds Ic of Table 3 were obtained in a similar manner.

TABLE 3

(Ic) — structure: 7-chloroquinoline with R¹ at 3-position and C(=Z)-Y at 8-position

| Example No. Compound No. | R¹ | —C=Z / Y | Mp. [°C.] |
|---|---|---|---|
| 29 | CH₃ | N—N, O, C₂H₅ (oxadiazole ring) | 150 |
| 30 | Cl | N—N, O (oxadiazole ring) | 218 |
| 31 | Cl | N—N, O, C₂H₅ (oxadiazole ring) | 131 |

EXAMPLE 32

5-(3,7-Dichloroquinol-8-yl)-1,3,4-oxadiazole-2-carboxamide 26.0 g (80 millimoles) of compound No. 4 in 100 g of polyphosphoric acid were stirred for 6 hours at 130° C., after which the mixture was stirred into water and left to crystallize overnight. 16.3 g (66%) of a product of melting point 220° C. (decomposition) were obtained (compound No. 32).

EXAMPLE 33

5-(3,7-Dichloroquinol-8-yl)-1,3,4-oxadiazol-2-one 12.8 g (50 millimoles) of 3,7-dichloroquinoline-8-carboxylic hydrazide (compound No. 1) were suspended in 100 ml of dimethoxyethane, 7.9 g (100 millimoles) of pyridine were added and phosgene was then passed in over a period of 4 hours at 25° C. Excess phosgene and the solvent were removed, the residue was stirred into water and the mixture was filtered under suction to give 8.7 g (62%) of a product of melting point of 87° C. (compound No. 33).

The 3-methyl derivative was obtained in a similar manner. Mp.: 232° C. (compound No. 34).

EXAMPLE 35

4,5-Dihydro-2-(3,7-dichloroquinol-8-yl)-oxazole 20.9 g (80 millimoles) of compound No. 14 in 50 ml of thionyl chloride were refluxed for 4 hours. The mixture was precipitated on ice, and 18.3 g (86%) of a product of melting point 145° C. were obtained (compound No. 35).

The compounds Ic listed in Table 4 were prepared in a similar manner.

TABLE 4

Structure (Ic): 7-chloroquinoline with R¹ at 3-position and C=Z/Y substituent at 8-position

| Example No. Compound No. | R¹ | —C=Z / Y | Mp. [°C.] |
|---|---|---|---|
| 36 | Cl | N—C(CH₃)=... —O— (oxazoline with CH₃) | 150 |
| 37 | CH₃ | N—C(CH₃)=... —O— (oxazoline with CH₃) × HCl | 218 |
| 38 | CH₃ | N—CH=... —O— (oxazoline) × HCl | 220 |

EXAMPLE 39

3-(7-Chloro-3-methylquinol-8-yl)-1,2,4-triazole 13.8 (50 millimoles) of compound No. 21 were stirred with 3.0 g (60 millimoles) of hydrazine hydrate in 50 ml of glacial acetic acid for 4 hours at 70° C. After precipitation from water and filtration under suction, 9.5 g (78%) of a product of melting point 274°–276° C. were isolated (compond No. 39).

Compound Ic in Table 5 was prepared in a similar manner.

TABLE 5

Structure (Ic): 7-chloroquinoline with R¹ at 3-position and C=X/Y substituent at 8-position

| Example No. Compound No. | R¹ | —C=X / Y | Mp. [°C.] |
|---|---|---|---|
| 40 | Cl | N—C=... N—N—H (triazole) | 280 |
| 41 | Cl | N—C(CH₃)=... N—N—H (with CH₃) | 218 |
| 42 | Cl | N—C(CH₃)=... O—N (isoxazoline with CH₃) | 125 |
| 43 | CH₃ | N—C(CH₃)=... O—N (isoxazoline with CH₃) | 145 |
| 44 | CH₃ | N—C(CH₃)=... N—N—H (with CH₃) | 238 |

3,7-Dichloroquinoline-8-hydroxamoyl chloride hydrochloride

Chlorine was passed into a suspension of 48.2 g (0.2 mole) of 3,7-dichloroquinoline-8-aldoxime in chloroform for 3 hours at 40° C., the suspension was filtered under suction and the residue was washed with ether and dried to give 59.3 g (95%) of a product of melting point >300° C. (compound No. 45).

3,7-Dichloroquinoline-8-hydroxamoyl bromide hydrobromide (compound No. 46) was obtained in a similar manner.

EXAMPLE 47

3,7-Dichloroquinoline-8-nitrile oxide 15.6 g (50 millimoles) of compound No. 45 were stirred into 100 ml of 10% strength sodium carbonate solution, stirred for 2 hours at room temperature and filtered under suction to give 108 g (90%) of a product of melting point 185° C. (compound No. 47).

The nitrile oxide can be obtained from compound No. 46 in a similar manner.

EXAMPLE 48

Dimethyl 3-(3',7'-dichloroquinolin-8'-yl)-1,2-oxazole-4,5-dicarboxylate 12.0 g (50 millimoles) of 3,7-dichloroquinoline-8-nitrile oxide (compound No. 47) were suspended in 100 ml of dimethoxyethane, 8.50 g (60 ml) of dimethyl acetylenedicarboxylate were added and the mixture was refluxed for 4 hours. Precipitation on water, filtration under suction and drying gave 17.8 g (93%) of a product of melting point 135° C. (compound No. 48).

The compounds Id listed in Table 6 were obtained in a similar manner.

TABLE 6

Structure (Id): 3,7-dichloroquinoline with C=X / Y substituent at position 8

| Example No. Compound No. | Y–C(=)–X | Mp. [°C.] |
|---|---|---|
| 49 | N—O, =CH-CH₂-CH(OC₂H₅) with methyl | 145 |
| 50 | N—O, with cyclopentane bearing N(CH₂)₄ | 105 |
| 51 | N—O, with CH(CH₃)(CO₂CH₃) side chain | 229 |
| 52 | N—O, with tetrahydropyran ring | 135 |
| 53 | N—O, CH₂-CH(CO₂CH₃) | 135 |
| 54 | N—O, with tetrahydrofuran-methyl | 125 |
| 55 | N—O, with tetrahydropyran | 164 |
| 56 | N—O, CH(CO₂CH₃)-CH(CO₂CH₃) | 78 |
| 57 | N—O, =C(NH₂)(NC) | 200 |
| 58 | NH—O, =C(CH₃)-C(CO₂CH₃)=C-O | 180 |

EXAMPLE 59

Carboxymethylthio 3,7-dichloroquinoline-8-hydroxamate 12.0 g (50 millimoles) of 3,7-dichloroquinoline-8-nitrile oxide (compound No. 47) were suspended in 100 ml of dimethoxyethane, and 5.6 g (60 millimoles) of mercaptoacetic acid were added. The mixture was stirred for 6 hours at room temperature, after which it was freed from the solvent, water was added and the mixture was filtered under suction. 13.5 g (81%) of a product of melting point of 174° C. were obtained (compound No. 59).

The compounds Ie listed in Table 7 were obtained similarly.

TABLE 7

Structure (Ie): 3,7-dichloroquinoline with C(X)=N-OH substituent at position 8

| Example No. Compound No. | X | Mp. [°C.] |
|---|---|---|
| 60 | NH₂ | 112 |
| 61 | OCH₃ | 130 |

EXAMPLE 62

3,7-Dichloro-8-propionylquinoline

A solution of a Grignard reagent, prepared from 7.2 g (60 millimoles) of ethyl bromide and 1.6 g (60 millimoles) of magnesium turnings in 30 ml of absolute tetrahydrofuran, was added dropwise, at −70° C., to a suspension of 6.4 g (25 millimoles) of methyl 3,7-dichloroquinoline-8-carboxylate in 25 ml of absolute tetrahydrofuran, and the mixture was slowly brought to room temperature. It was then poured onto ice and acidified with 10% strength hydrochloric acid, and the product was filtered off under suction and dried. 4.5 g (71%) of a product of melting point 108°–110° C. were obtained (compound No. 62).

7-Chloro-3-methyl-8-propionylquinoline (compound No. 63) was obtained similarly.

EXAMPLE 64

Ethyl 3-(7'-chloro-3'-methylquinol-8'-yl)-propan-3-one carboxylate 70.8 g (0.3 mole) of methyl 7-chloro-3-methylquinoline-8-carboxylate were suspended in 150 ml of ethyl acetate, 16 g of 80% strength sodium hydride were added, and the mixture was refluxed for 5 hours. The mixture was precipitated on ice and acidifed with dilute hydrochloric acid, after which the product was filtered off under suction and dried. 51 g (58%) of a product of melting point 143°–145° C. were obtained (compound No. 64).

Use Examples

The herbicidal action of the substituted quinoline-8-carboxamides of the formula I on plant growth is demonstrated in greenhouse experiments.

The vessels employed were plastic flowerpots having a volume of 300 cm$^3$, and which were filled with a sandy loam containing about 3.0% humus. Peat was added to the soybean plants to give a better stand. The seeds of the test plants were sown separately, according to species. For the preemergence treatment, the active ingredients were applied to the surface of the soil immediately after the seeds had been sown. The compounds were emulsified or suspended in water as vehicle, and sprayed through finely distributing nozzles. The application rates were 0.5 and 2.0 kg of active ingredient per hectare. After the agents had been applied, the vessels were lightly sprinkler-irrigated to induce germination and growth. Transparent plastic covers were then placed on the vessels until the plants had taken root. The cover ensured uniform germination of the plants, insofar as this was not impaired by the active ingredients.

For the postemergence treatment, the plants were first grown in the vessels to a height of from 3 to 15 cm, depending on growth form, before being treated. For this treatment, either plants which had been sown directly in the pots and grown there were selected, or plants which had been grown from seedlings and were transplanted to the pots a few days before treatment. The application rates for postemergence treatment were 2.0 and 3.0 kg of active ingredient per hectare. No covers were placed on the pots in this method.

The pots were set up in the greenhouse—species from warmer areas at from 20° to 36° C., and species from moderate climates at 10° to 20° C. The experiments were run for 2 to 4 weeks. During this period, the plants were tended and their reactions to the various treatments assessed.

The plant species used in the experiments were *Avena sativa, Cassia tora, Centaurea cyanus, Echinochloa crus-galli, Galium aparine, Glycine max., Ipomoea spp., Oryza sativa, Veronica spp.,* and *Zea mays.*

On postemergence application of 3.0 kg/ha, the herbicidal action of compounds nos. 1 and 7, for instance, on unwanted dicotyledonous plants significantly exceeded that of prior art active ingredient A (Example 34 in European No. 60,429).

Compounds 4 and 10 were suitable for combating *Galium aparine* postemergence at a rate of 3.0 kg/ha without causing any damage to oats.

Compound 7 was used postemergence to combat selected dicotyledonous and monocotyledonous plants. At a rate of 2.0 kg/ha, neither soybean nor rice plants exhibited any appreciable damage, and *Echinochloa crus-galli* and *Cassia tora* were excellently controlled.

On preemergence application, compound 1 (at 0.5 kg/ha) and compound 7 (at 2.0 kg/ha) had a strong herbicidal action on unwanted dicotyledonous plants. Indian corn plants remained undamaged.

On preemergence application too, compound 7 proved suitable for combating injurious plants such as *Echinochloa crus-galli* and Ipomoea; soybean plants remained undamaged.

Compound 32 was suitable both pre- and postemergence at 1.0 kg/ha for combating *Echinochloa crus-galli* and *Veronica spp.;* wheat plants were only damaged slightly, if at all.

We claim:

1. A quinoline derivative of the formula

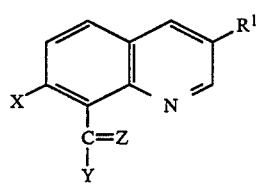

where $R^1$ is halogen or $C_1$–$C_4$-alkyl, X is halogen, Z is oxygen Y is a radical —$NR^2R^3$, in which $R^2$ is hydrogen and $R^3$ is $C_1$–$C_4$-alkoxy, or Y is a hydrazino radical which is unsubstituted or substituted by $C_2$–$C_5$-alkylcarbonyl, $C_2$–$C_5$-alkoxycarbonyl or $C_1$–$C_4$-alkyl which is unsubstituted or substituted by $C_2$–$C_5$-alkoxycarbonyl.

2. A quinoline derivative of the formula I as set forth in claim 1, where Y is the radical —$NHR^3$ and $R^3$ is $C_1$–$C_4$-alkoxy.

3. A quinoline derivative of the formula I as set forth in claim 1, where $R^1$ is chlorine, X is chlorine, Y is the radical —$NHR^3$ and $R^3$ is ethoxy.

4. A quinoline derivative of the formula I as defined in claim 1,

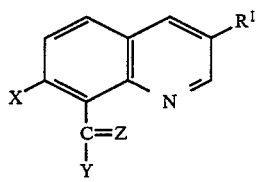

wherein Y is —NH—$NH_2$.

5. A quinoline derivative of the formula I as defined in claim 1,

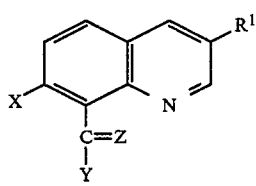

wherein Y is a hydrazino radical, which is substituted by $C_2$–$C_5$-alkylcarbonyl or $C_2$–$C_5$-alkoxycarbonyl or $C_2$–$C_5$-alkoxycarbonyl or $C_1$–$C_4$-alkyl which is unsubstituted or substituted by $C_2$–$C_5$-alkoxycarbonyl.

6. A quinoline derivative of the formula I as defined in claim 1,

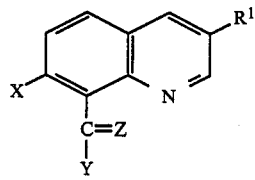

(I)

wherein R[1] is chlorine, X is chlorine and Y is —NH—NH$_2$.

7. A process for combatting the growth of unwanted plants, wherein the unwanted plants and/or the area to be kept free from unwanted plant growth are treated with a herbicidally effective amount of a quinoline derivative of the formula I as set forth in claim 1.

8. The process of claim 7, wherein R[1] of the quinoline derivative is chlorine, X is chlorine and Y is —NHR[3] where R[3] is ethoxy.

* * * * *